US006755846B1

(12) United States Patent
Yadav

(10) Patent No.: US 6,755,846 B1
(45) Date of Patent: *Jun. 29, 2004

(54) VASCULAR FILTER

(75) Inventor: Jay S. Yadav, Roswell, GA (US)

(73) Assignee: Angioguard, Inc., Plymouth, MN (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

This patent is subject to a terminal disclaimer.

(21) Appl. No.: 09/155,753

(22) PCT Filed: Feb. 3, 1998

(86) PCT No.: PCT/US98/01894

§ 371 (c)(1),
(2), (4) Date: Oct. 2, 1998

(87) PCT Pub. No.: WO98/33443

PCT Pub. Date: Aug. 6, 1998

Related U.S. Application Data

(63) Continuation-in-part of application No. 08/794,011, filed on Feb. 3, 1997, now abandoned.

(51) Int. Cl.[7] .............................................. A61M 29/00
(52) U.S. Cl. ...................................................... 606/200
(58) Field of Search ........................... 606/200, 1, 159, 606/198

(56) References Cited

U.S. PATENT DOCUMENTS

| 3,435,824 A | 4/1969 | Gamponia |
| 3,889,685 A | 6/1975 | Miller, Jr. et al. |
| 3,952,747 A | 4/1976 | Kimmel, Jr. |

(List continued on next page.)

FOREIGN PATENT DOCUMENTS

| EP | 737450 | 10/1996 |
| EP | 1 179 321 A | 2/2002 |
| GB | 2020557 | 11/1979 |
| WO | WO 96/01591 | 1/1996 |
| WO | WO 02/056955 A | 7/2002 |

OTHER PUBLICATIONS

A. Cragg et al., A New Percutaneous Vena Cava Filter, *AJR*, 141, Sep. 1983, pp. 601–604.

A. Cragg et al., Nonsurgical Placement of Arterial Endoprosthesis: A New Technique Using Nitinol Wire, *AJR*, Apr. 1983, pp. 261–263.

G. Lund et al., Long–Term Patency of the Ductus Arteriosus After Balloon Dilatation: An Experimental Study, *AJR*, Sep. 1983, p. 772.

M. H. Wholey et al., PTA and Stends in the Treatment of Extracanial Circulation, *Journal of Advanced Cardiology*, vol. 8, Suppl. E. 1996, pp. 25E–30E.

(List continued on next page.)

*Primary Examiner*—Michael H. Thaler

(57) ABSTRACT

A removable vascular filter device for blocking micro-and macro-emboli while allowing continued perfusion of blood, comprises a guidewire having distal and proximal portions, wherein there is a recess in the distal portion and a filter comprising a flexible filter membrane and a filter membrane support structure. The filter membrane has a fixed inner portion and a free outer portion, wherein the filter membrane fixed inner portion is movably attached toward the distal end of the guidewire recess and wherein the filter membrane free outer portion is positioned in the recess when the filter membrane is in a collapsed state. A deploying means causes the filter membrane proximal end portion to assume a position substantially normal to the longitudinal axis of the guidewire.

20 Claims, 14 Drawing Sheets

U.S. PATENT DOCUMENTS

| | | |
|---|---|---|
| 4,230,119 A | 10/1980 | Blum |
| 4,349,029 A | 9/1982 | Mott |
| 4,425,908 A | 1/1984 | Simon |
| 4,494,531 A | 1/1985 | Gianturco |
| 4,545,390 A | 10/1985 | Leary |
| 4,619,246 A | 10/1986 | Molgaard-Neilsen et al. |
| 4,619,274 A | 10/1986 | Morrison |
| 4,688,553 A | 8/1987 | Metals |
| 4,706,671 A | 11/1987 | Weinrib |
| 4,723,549 A | 2/1988 | Wholey et al. |
| 4,727,873 A | 3/1988 | Mobin-Uddin |
| 4,781,177 A | 11/1988 | Lebigot |
| 4,790,812 A | 12/1988 | Hawkins, Jr. et al. |
| 4,790,813 A | 12/1988 | Kensey |
| 4,793,348 A | 12/1988 | Palmaz |
| 4,794,928 A | 1/1989 | Kletschka |
| 4,832,055 A | 5/1989 | Palestrant |
| 4,842,579 A | 6/1989 | Shiber |
| 4,873,978 A | 10/1989 | Ginsburg |
| 4,884,573 A | 12/1989 | Wajay et al. |
| 4,921,484 A | 5/1990 | Hillstead |
| 4,926,858 A | 5/1990 | Gifford, III et al. |
| 4,957,501 A | 9/1990 | Lahille et al. |
| 4,969,891 A | 11/1990 | Gewertz |
| 4,990,156 A | 2/1991 | Lefebvre |
| 5,011,488 A | 4/1991 | Ginsburg |
| 5,053,008 A | 10/1991 | Bajaj |
| 5,059,205 A | 10/1991 | El-Nounou et al. |
| 5,092,839 A | 3/1992 | Kipperman |
| 5,095,915 A | 3/1992 | Engelson |
| 5,108,419 A | 4/1992 | Reger et al. |
| 5,133,733 A | 7/1992 | Rasmussen et al. |
| 5,152,777 A | 10/1992 | Goldberg et al. |
| 5,190,540 A | 3/1993 | Lee |
| 5,190,546 A | 3/1993 | Jervis |
| 5,201,757 A | 4/1993 | Heyn et al. |
| 5,242,462 A | 9/1993 | El-Nounou et al. |
| 5,279,546 A | 1/1994 | Mische et al. |
| 5,324,304 A | 6/1994 | Rasmussen |
| 5,329,942 A | 7/1994 | Gunther et al. |
| 5,413,586 A | 5/1995 | Dibie et al. |
| 5,421,832 A | 6/1995 | Lefebvre |
| 5,496,277 A | 3/1996 | Termin et al. |
| 5,531,788 A | 7/1996 | Dibie et al. |
| 5,549,626 A | 8/1996 | Miller et al. |
| 5,632,760 A | 5/1997 | Sheiban et al. |
| 5,662,631 A | 9/1997 | Marx |
| 5,662,671 A | 9/1997 | Barbut et al. |
| 5,681,347 A | 10/1997 | Cathcart et al. |
| 5,695,519 A | 12/1997 | Summers et al. |
| 5,709,704 A | 1/1998 | Nott et al. |
| 5,749,890 A | 5/1998 | Shaknovich |
| 5,769,816 A | 6/1998 | Barbut et al. |
| 5,779,716 A | 7/1998 | Cano et al. |
| 5,807,398 A | 9/1998 | Shaknovich |
| 5,810,874 A | 9/1998 | Lefebvre |
| 5,814,064 A | 9/1998 | Daniel et al. |
| 5,827,324 A | 10/1998 | Cassell et al. |
| 5,836,969 A | 11/1998 | Kim et al. |
| 5,848,964 A | 12/1998 | Samuels |
| 5,876,367 A | 3/1999 | Kaganov et al. |
| 5,902,263 A | 5/1999 | Patterson et al. |
| 5,910,154 A | 6/1999 | Tsugita et al. |
| 6,001,118 A | 12/1999 | Daniel et al. |
| 6,013,093 A | 1/2000 | Nott et al. |
| 6,051,014 A | 4/2000 | Jang |
| 6,053,932 A | 4/2000 | Daniel et al. |
| 6,059,814 A | 5/2000 | Ladd |
| 6,059,825 A | 5/2000 | Hobbs et al. |
| 6,068,621 A | 5/2000 | Balceta et al. |
| 6,074,357 A | 6/2000 | Kaganov et al. |
| 6,080,178 A | 6/2000 | Meglin |
| 6,126,673 A | 10/2000 | Kim et al. |
| 6,152,946 A | 11/2000 | Broome et al. |
| 6,165,179 A | 12/2000 | Cathcart et al. |
| 6,165,200 A | 12/2000 | Tsugita et al. |
| 6,168,604 B1 | 1/2001 | Cano |
| 6,179,859 B1 | 1/2001 | Bates et al. |
| 6,179,861 B1 | 1/2001 | Khosravi et al. |
| 6,187,015 B1 | 2/2001 | Brenneman |
| 6,203,561 B1 | 3/2001 | Ramee et al. |
| 6,214,025 B1 | 4/2001 | Thistle et al. |
| 6,221,096 B1 | 4/2001 | Aiba et al. |
| 6,241,746 B1 | 6/2001 | Bosma et al. |
| 6,258,115 B1 | 7/2001 | Dubrul |
| 6,267,776 B1 | 7/2001 | O'Connell |
| 6,267,777 B1 | 7/2001 | Bosma et al. |
| 6,270,513 B1 | 8/2001 | Tsugita et al. |
| 6,273,900 B1 | 8/2001 | Nott et al. |
| 6,277,138 B1 | 8/2001 | Levinson et al. |
| 6,280,432 B1 | 8/2001 | Turovskiy et al. |
| 6,290,710 B1 | 9/2001 | Cryer et al. |
| 6,336,934 B1 | 1/2002 | Gilson et al. |
| 6,346,116 B1 | 2/2002 | Brooks et al. |

OTHER PUBLICATIONS

Eichelter, et al., "Prophylaxis of Pulmonary Embolism," *Archives of Surgery*, vol. 97, Aug. 1968, pp. 348 et seq.

Greenfield, et al., "A New Intercaval Filter Permitting Continued Flow and Resolution of Emboli," *Surgery*, vol. 73, No. 4, pp. 599–606.

European Search Report for corresponding Applicatio No. EP 03 25 1112, dated May 28, 2003.

Topol, Eric J., et al. Recognition of the Importance of Embolization in Atherosclerotic Vascular Disease American Heart Journal 2000.

VASCULAR FILTER

This application is a continuation-in-part of commonly assigned U.S. patent application Ser. No. 08/794,011, filed Feb. 3, 1997 now abandoned.

FIELD OF THE INVENTION

The present invention relates to the treatment of vascular disease of either surgery or percutaneous angioplasty and stenting. More particularly, the invention relates to a device that reduces macro- and micro-embolism during the treatment of vascular stenosis.

BACKGROUND OF THE INVENTION

A variety of surgical and non-surgical angioplasty procedures have been developed for removing obstructions from blood vessels. Balloon angioplasty utilizes a balloon-tipped catheter which may be inserted within a stenosed region of the blood vessel. By inflation of the balloon, the stenosed region is dilated. Surgery involves either removing the plaque from the artery or attaching a graft to the artery so as to bypass the obstructing plaque. Other techniques, such as atherectomy, have also been proposed. In atherectomy, a rotating blade is used to shave plaque from an arterial wall.

One problem common with all of these techniques is the accidental release of portions of the plaque or thrombus, resulting in emboli which can lodge elsewhere in the vascular system. Such emboli are, of course, extremely dangerous to the patient, frequently causing severe impairment of the distal circulatory bed. Depending upon the vessel being treated, this may result in a stroke or myocardial infarction or limb ischemia.

Vascular filters or embolism traps for implantation into the vena cava of a patient are well known, being illustrated by, for example, U.S. Pat. Nos. 4,727,873 and 4,688,553. Additionally, there is a substantial amount of medical literature describing various designs of vascular filters and reporting the results of the clinical and experimented use thereof. See, for example, the article by Eichelter & Schenk entitled "Prophylaxis of Pulmonary Embolism," Archives of Surgery, Vol. 97, August 1968, pp. 348 et seq. See, also, the article by Greenfield, et al., entitled "A New Intracaval Filter Permitting Continued Flow and Resolution of Emboli", Surgery, Vol. 73, No. 4, pp. 599–606 (1973).

Vascular filters are used, often during a postoperative period, when there is a perceived risk of a patient encountering a pulmonary embolus resulting from clots generated at the surgical site or the like. As a typical use of vascular filters, the filter is mounted in the vena cava to catch large emboli passing from the surgical site to the lungs.

The vascular filters of the prior art are usually permanently implanted in the venous system of the patient, so that even after the need for the filter has abated, the filter remains in place for the lifetime of the patient, absent surgical removal. U.S. Pat. No. 3,952,747 describes a stainless steel filtering device which is permanently implanted transvenously within the inferior vena cava. The filtering device is intended to treat recurrent pulmonary embolism. U.S. Pat. No. 4,873,978 describes a catheter device comprising a catheter body having a strainer mounted at it distal end. The strainer is shiftable between an opened configuration where it extends substantially across the blood vessel to entrap passing emboli, and a closed configuration where it retains the captured emboli during removal of the catheter. A mechanism actuable at the proximate end of the catheter body allows selective opening and closing of the strainer. Typically, the strainer is a collapsible cone having an apex attached to a wire running from the distal end to the proximate end of the catheter body.

Permanent implantation is often deemed medically undesirable, but it has been done because vascular filters are implanted in patients primarily in response to potentially life threatening situations. Accordingly, the disadvantages of permanent implantations of a vascular filter are often accepted.

To avoid permanent implantation, it would be highly desirable to provide an apparatus and method for preventing embolisms associated with conventional surgery and angioplasty procedures. In particular, it would be desirable to provide a device which could be located within the vascular system to collect and retrieve portions of plaque and thrombus which have dislodged during the surgery or angioplasty procedure.

OBJECT OF THE INVENTION

It is an object of this invention to provide a vascular filter for reducing macro- and micro-embolism.

It is also an object of the invention to provide a vascular filter which is readily removable from the vascular system, or elsewhere, of a patient when the filter is no longer needed.

It is a further object of the invention to provide a vascular filter having a configuration which does not require hooks to penetrate and grip the blood vessel walls, so that the implantation results in less blood vessel injury.

It is a yet further object of the invention to provide a vascular filter of very low profile which is part of a guidewire and can be used in small vessels These and other objects of the invention will become more apparent from the description below.

SUMMARY OF THE INVENTION

The present invention generally relates to the surgical and interventional treatment of vascular disease. For example, during angioplasty and stenting of carotid stenosis, there is occurrence of macro- and micro-embolism which increases the risk of a minor or major stroke. The device of the present invention for reducing macro- and micro-embolism is very useful in helping to prevent the risk of stroke. However, this device would also be useful in any angioplasty or surgical procedure where embolization is a risk.

The filters of the present invention will decrease embolism while allowing brain, or other distal tissue, perfusion. The filters are incorporated into a guidewire which is used for the entire procedure from crossing a lesion to deploying a stent. The filter consists of a thin membrane attached to the guidewire and supported by fine metal spines. The filter membrane has a pore size such that blood flow is not impeded when the filter membrane is expanded but micro- and macro-emboli are blocked. The attachments of the filter membrane to the guidewire allow expansion of the filter membrane with a firm fit inside the artery. Expansion of the filter membrane is aided by the forward flow of blood against the filter. The attachments also allow for collapse of the filter membrane at the end of the procedure so it fits tightly against the guidewire and can be withdrawn through the guide catheter. The filter design results in a very low profile so that the initial crossing of the lesion is minimally traumatic. Also, the small diameter and small profile facilitate use of the device in small or larger arteries with minimal or no obstruction of blood flow.

BRIEF DESCRIPTION OF THE DRAWINGS

The above and other objects and advantages of the invention will be apparent upon consideration of the following detailed description, taken in conjunction with the accompanying drawings, in which the reference characters refer to like parts throughout and in which.

DETAILED DESCRIPTION OF THE INVENTION

The present invention relates to a vascular filter for use in percutaneous angioplasty and stenting and provides for the prevention of distal embolism during endovascular procedures. Further, the filter device of the invention allows for distal perfusion while preventing embolism.

The device consists of a thin, perforated filter membrane which is capable of blocking emboli and which is attached to the distal end of a guidewire. The device preferably uses thin fibers which are moveable and are attached to the filter membrane to deploy and collapse the filter membrane. The invention also contemplates the use of metal spines or inflatable spines attached to the filter membrane to deploy the filter membrane. The fibers or spines can also be attached to a moveable core which is slidable within the guidewire and is used to deploy and collapse the filter membrane.

The filter membrane deploys in an umbrella-like fashion with the unattached edge of the membrane moving upward, i.e., distally, and outward until it is in firm contact with an artery wall. When the filter membrane is deployed, it spans the cross-sectional area of the vessel lumen being treated for a stenosis such as carotid stenosis, or another condition likely to produce emboli.

Figure 1:
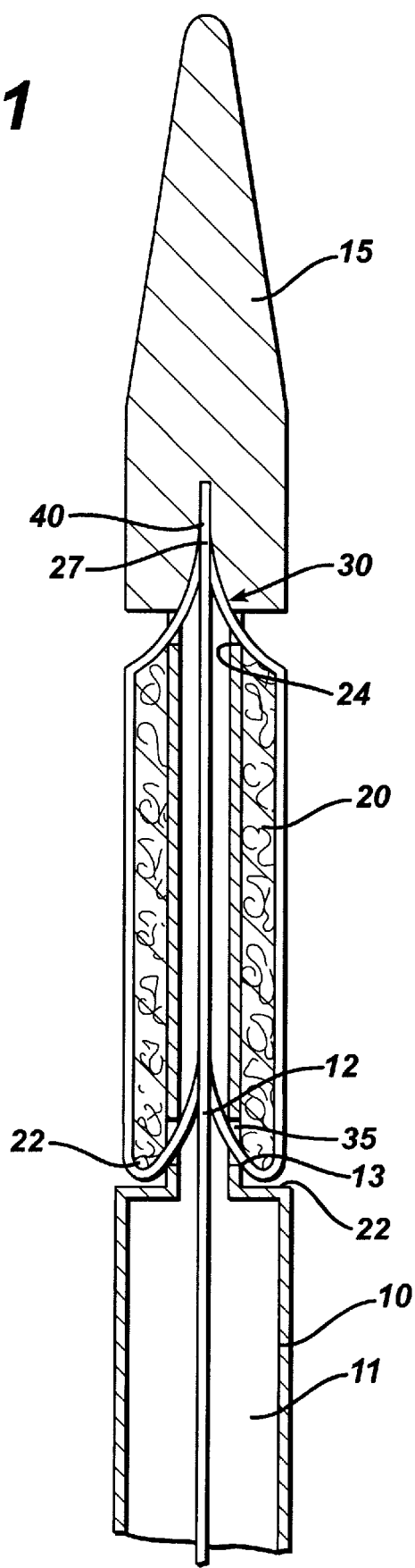
FIG. 1 is a lateral, partly cross-sectional view of the distal end of a guidewire of one embodiment of the invention with the filter membrane in a collapsed position.

The invention can perhaps be appreciated better by referring to the drawings. FIG. 1 illustrates a lateral, cross-sectional view of a distal end of a guidewire 10 with a filter membrane 20 attached thereto. FIG. 1 shows guidewire 10 with a shapeable, tapered soft tip 15 at its extreme distal end which provides flexibility and maneuverability to guidewire 10. The filter membrane in FIG. 1 is in a collapsed position. Filter membrane 20 has a fixed portion 24 which is movably attached to guidewire 10, and filter membrane 20 lies in a recess in guidewire 10 proximal to fixed portion 24 when filter membrane 20 is in the collapsed state. As seen in FIG. 1, the filter membrane 20 in the collapsed state has an outside diameter that is less than the outside diameter of any portion of guidewire 10 except for the recess and the distal portion of distal tip 15. A moveable core 40 runs through a center lumen 11 of guidewire 10 and preferably extends distally a short distance beyond fixed portion 24 of filter membrane 20. Deploying wires or fibers 30 are each firmly attached at one end 27 to moveable core 40 distal to fixed portion 21 of filter membrane 20. The deploying fibers 30 are attached at their other ends to filter membrane 20 at attachment points 22.

Collapsing fibers 35 are each firmly attached at one end 12 to the portion of moveable core wire 40 which is interior to filter membrane 20 when it is in the collapsed state. Collapsing fibers 35 are each attached at their other end 13 to filter membrane 20 at attachment points 22. Accordingly, collapsing fibers 35 lie interior to filter membrane 20 when filter membrane 20 is in the collapsed state.

Filter membrane 20 is deployed when the operator pulls moveable core 40 proximally through the interior of guidewire 10. Prior to retraction of moveable core 40, deploying fibers 30 are sufficiently relaxed so as not to create any tension at filter membrane attachment points 22. Upon retraction of moveable core 40, tension is created in deploying fibers 30.

There-will preferably be from 2 to 6 each of evenly-spaced deploying fibers 30 and collapsing fibers 35, 3 or 4 being most preferred. The deploying fibers 30 and collapsing fibers 35 can be made of any flexible, medically acceptable material, including stainless steel, nitinol, or another metal or metallic alloy or a non-metallic substance such as graphite or a suitable polymer. In addition, guidewire 10 and moveable core 40 can be made from similar materials, as would be appreciated by those skilled in the art. Typically, guidewire could have an external diameter of from about 0.014 mm to about 0.035 mm, a wall thickness of from about 0.002 mm to about 0.010 mm, and a length of from about 25 cm to about 300 cm. Also, moveable core 40 could have a diameter of from about 0.003 mm to about 0.010 mm and a length of from about 30 cm to about 350 cm.

Figure 2:
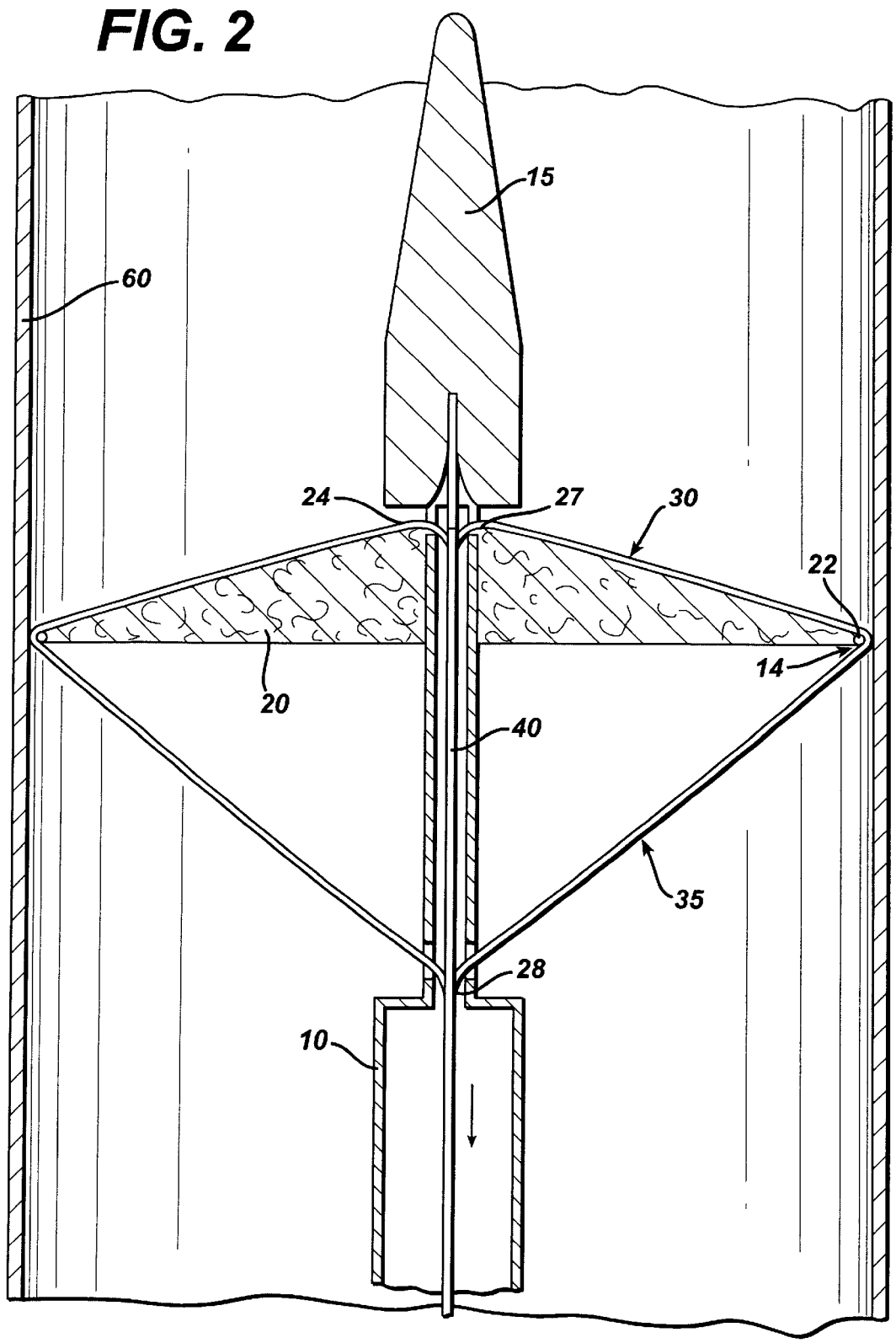
FIG. 2 is a lateral, partly cross-sectional view of the distal end of a guidewire of FIG. 1 with the filter membrane in an expanded, deployed position.

FIG. 2 illustrates the filter device of the invention in a deployed position on the inside of an artery wall 60. Moveable core 40 is in a retracted state, i.e., pulled proximally through the interior of guidewire 10. Tension is created in deploying fibers 30, and filter membrane 20 extends to a deployed position where the outer edge 14 of filter membrane 20 contacts artery wall 60. In this deployed position, collapsing fibers 35 are in a relaxed state and extend from filter membrane attachment points 22 to fixed attachment points 28 on moveable core 40.

The flow of blood in FIG. 2 is toward the distal end of guidewire 10. As such, the force of the flow of blood pushes on deployed filter membrane 20 and helps to maintain filter membrane 20 in the deployed position.

For withdrawal of guidewire 10 and the filter device, filter membrane 20 is collapsed so that it sits tightly against guidewire 10. This is accomplished by extending moveable core 40 distally through guidewire 10, thus relaxing deploying fibers 30 and creating tension in collapsing fibers 35. The tension in collapsing fibers 35 collapses the filter membrane 20, allowing it to fit tightly against guidewire 10 in recess 16 as depicted in FIG. 1.

Figure 3:
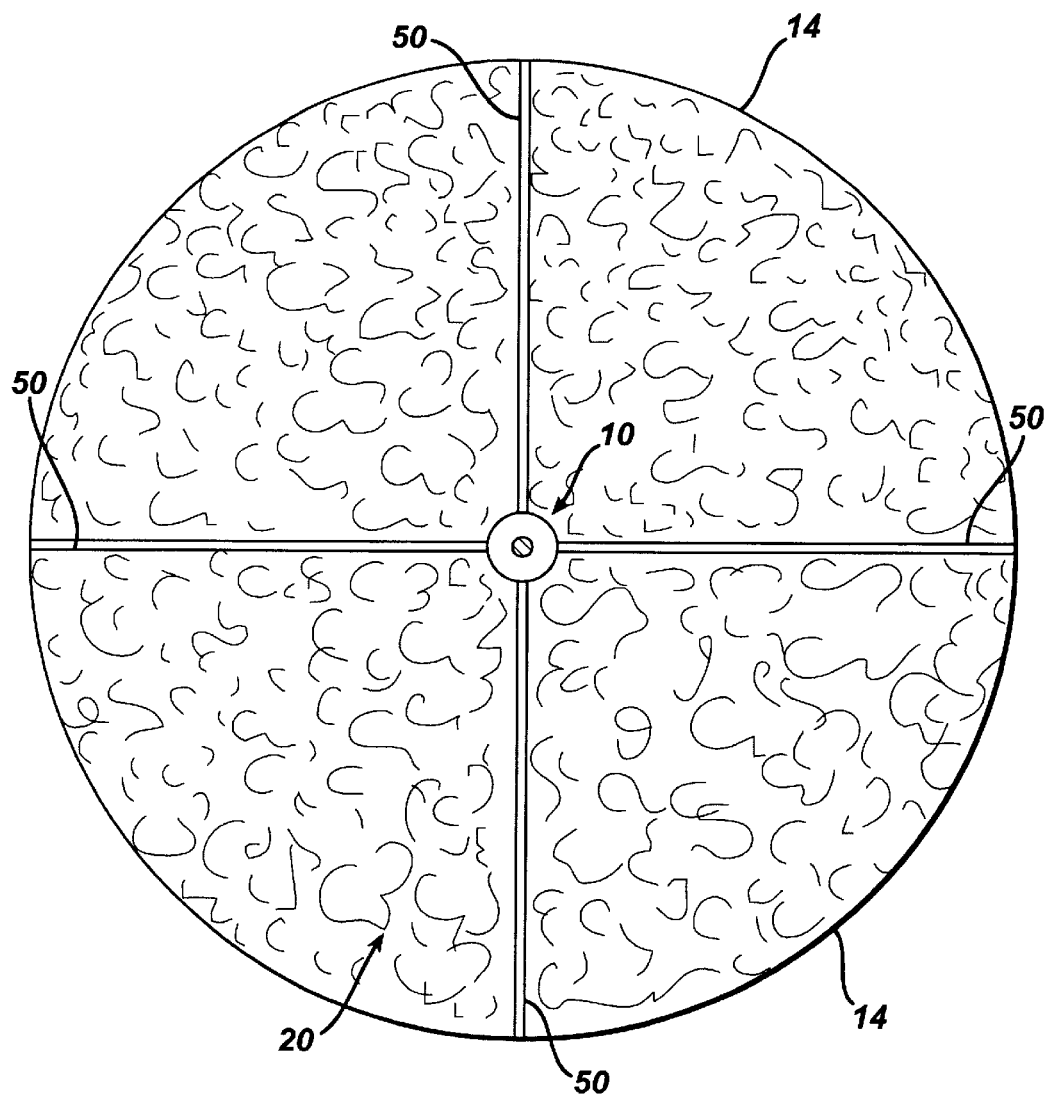
FIG. 3 is a proximal end-on view of the filter membrane shown in FIG. 2.

FIG. 3 illustrates the filter device of the invention from a distal end view in FIG. 2 with filter membrane 20 deployed. Guidewire 10 is centrally located, and structural wires 50 are seen extending from guidewire 10 to the outer edge 14 of filter membrane 20. These wires 50 provide structural integrity and rigidity to filter membrane 20. FIG. 3 depicts four, evenly-spaced structural wires 50, but there can be more or less structural wires 50. Preferably there are from two to six structural wires 50, which may be spaced regularly or irregularly. The wires 50 may preferably be comprised of stainless steel or another medically acceptable metal or alloy.

Filter membrane 20 of the invention is preferably a mesh such as that depicted in FIG. 3. The mesh should have pores of a size sufficient to block and capture any micro- and macro-emboli which may flow downstream from the site where the stenosis is being treated, but large enough such that blood flow is not impeded. The mesh used in the filter device of the invention can have a pore size of from about 20 to about 300 microns, preferably from about 30 to about 100 microns, more preferably from about 40 to 60 microns. Moreover, the size of filter membrane 20, i.e., the distance from guidewire 10 to free ends 22, is such as to allow a firm fit between filter membrane 20 and artery wall 60. The diameter of filter membrane 20 will be directly related to the artery being treated, with typical diameters ranging from about 2 mm to about 40 mm, most preferably from about 2 mm to about 20 mm.

The membrane can be comprised of fabric or non-fabric meshes, such as those used in known hemodialysis filters or heart-lung bypass machine filters. Suitable materials include polymers or physiologically acceptable metals or alloys.

Figure 4:
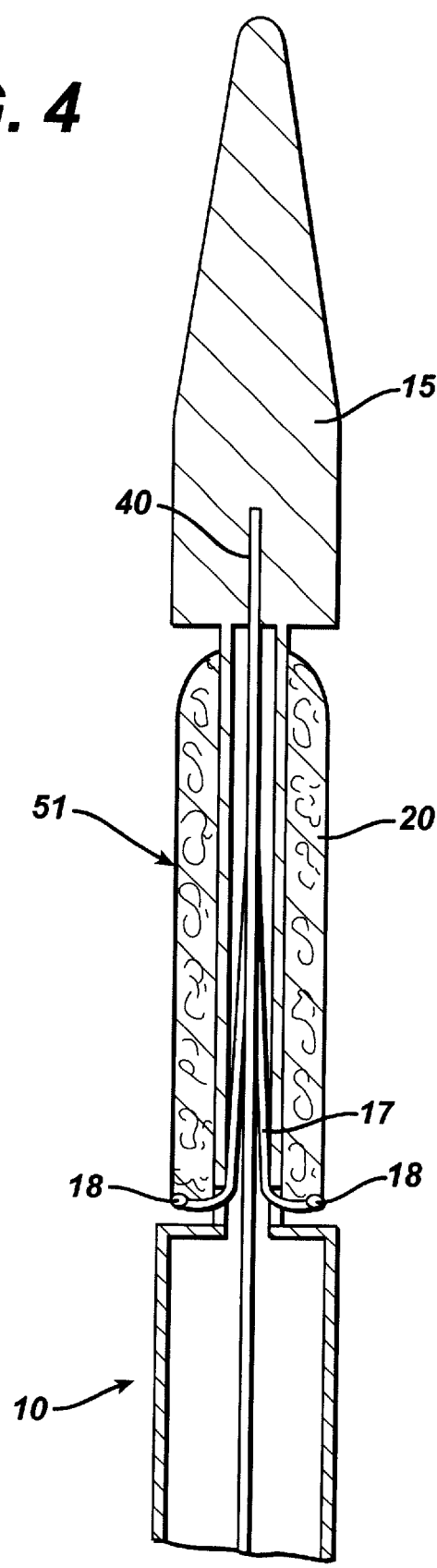
FIG. 4 is a lateral, partly cross-sectional view of another embodiment of the invention.
Figure 5A:
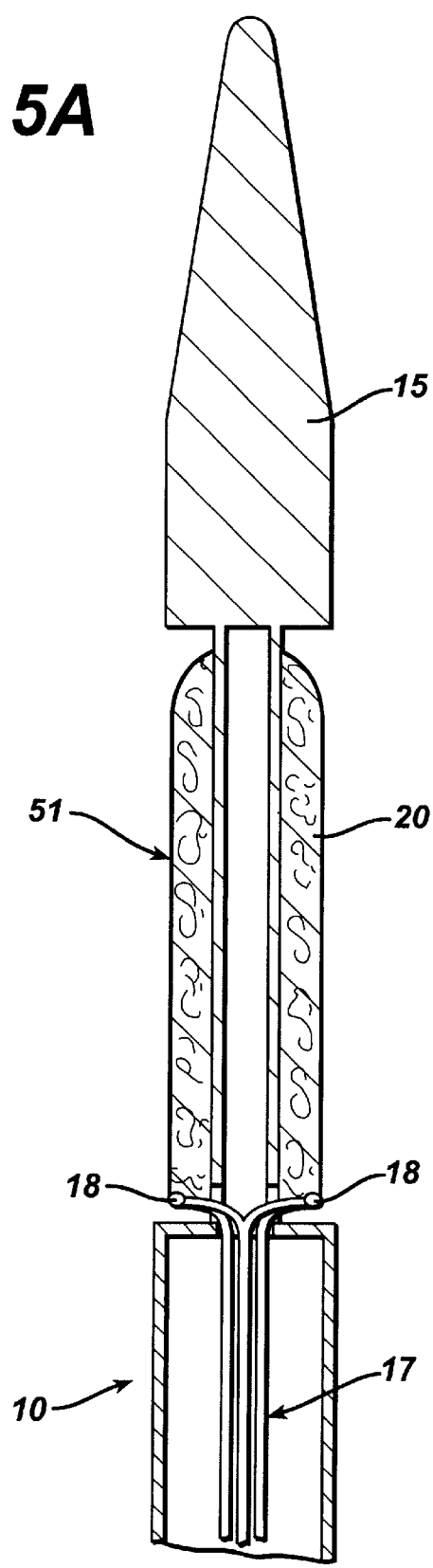
FIG. 5A is a lateral, partly cross-sectional view of a further embodiment of the invention.
Figure 5B:
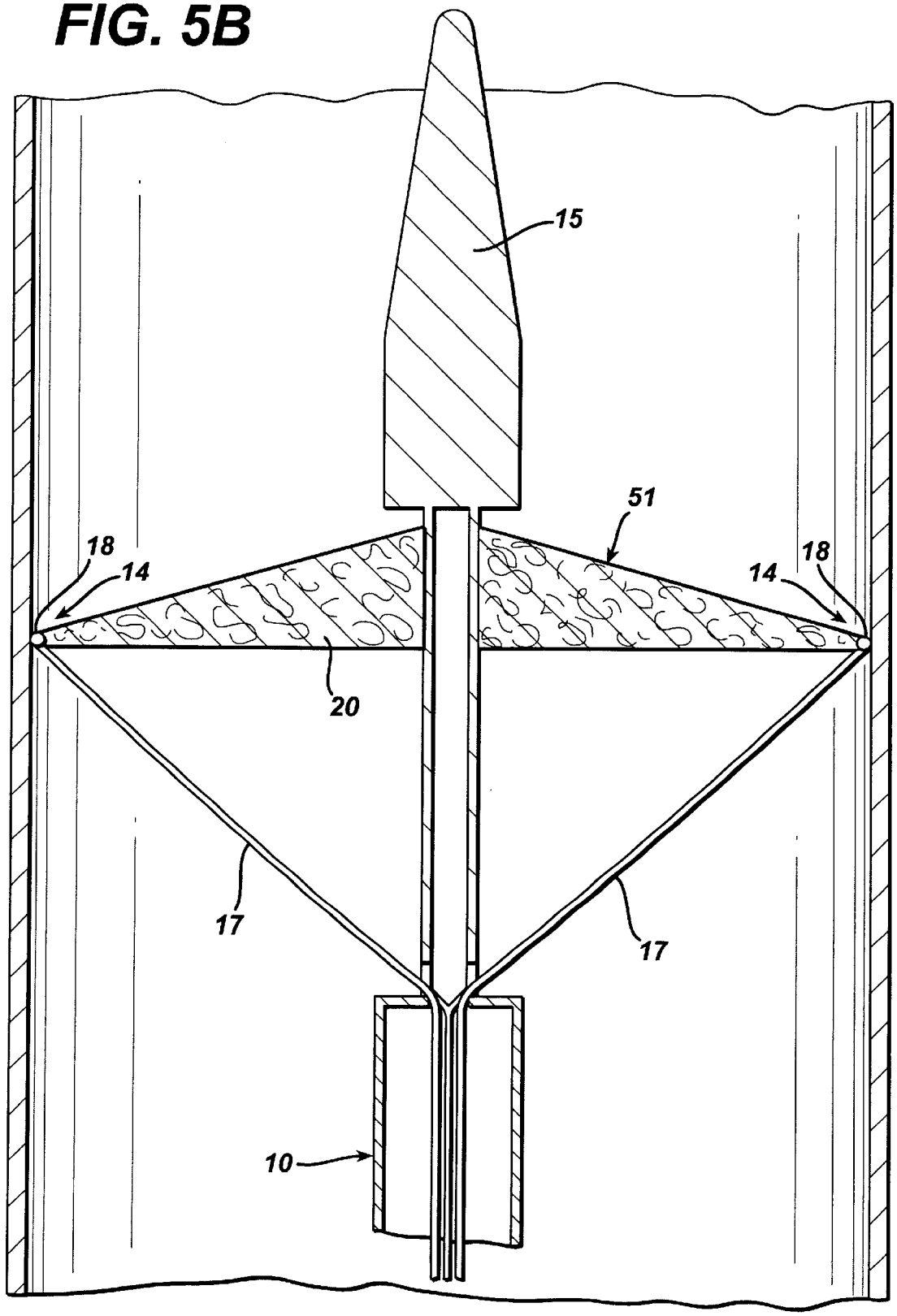
FIG. 5B is a lateral, partly cross-sectional view of the embodiment of the invention shown in FIG. 5A with the filter membrane in an expanded, deployed position.

In alternative embodiments of the invention shown in FIGS. 4, 5A and 5B, filter membrane 20 will be suspended between from two to six, preferably three or four, thin metal wires 51 which serve as spines for filter membrane 20. Wires 51 may be comprised of stainless steel or another metallic alloy, nitinol, or another shape-memory material. Wires 51 will be constructed so that they assume a 90° angle with guidewire 10 when they are in an unconstrained state. This will result in expansion of the filter membrane 20 to a position normal to guidewire 10. A set of thin fibers 17 are attached at attachment points 18 to filter membrane outer edge 14 and are used to collapse filter membrane 20.

FIG. 4 shows an embodiment of this invention in which metal wires 51 are allowed to regain their 90° angle unconstrained state by use of a moveable core 40 that runs through guidewire 10. Prior to retraction of moveable core 40, fibers 17 are sufficiently tensed so as to restrain wires 51. Upon retraction of moveable core 40, tension in fibers 17 is released and wires 51 are allowed to revert to their relaxed shape, which will result in expansion of filter membrane 20 to a position normal to guidewire 10.

FIGS. 5A and 5B show an embodiment of the invention wherein wires 51 are restrained by fibers 17 that run through guidewire 10 and that are controlled at a remote location. In FIG. 5A, there is sufficient tension in fibers 17 to maintain wires 51 in a constrained position. In FIG. 5B, tension in fibers 17 has been relaxed such that wires 51 are allowed to revert to their relaxed shape, which will result in expansion of filter membrane 20 to a position normal to guidewire 10.

Figure 6:
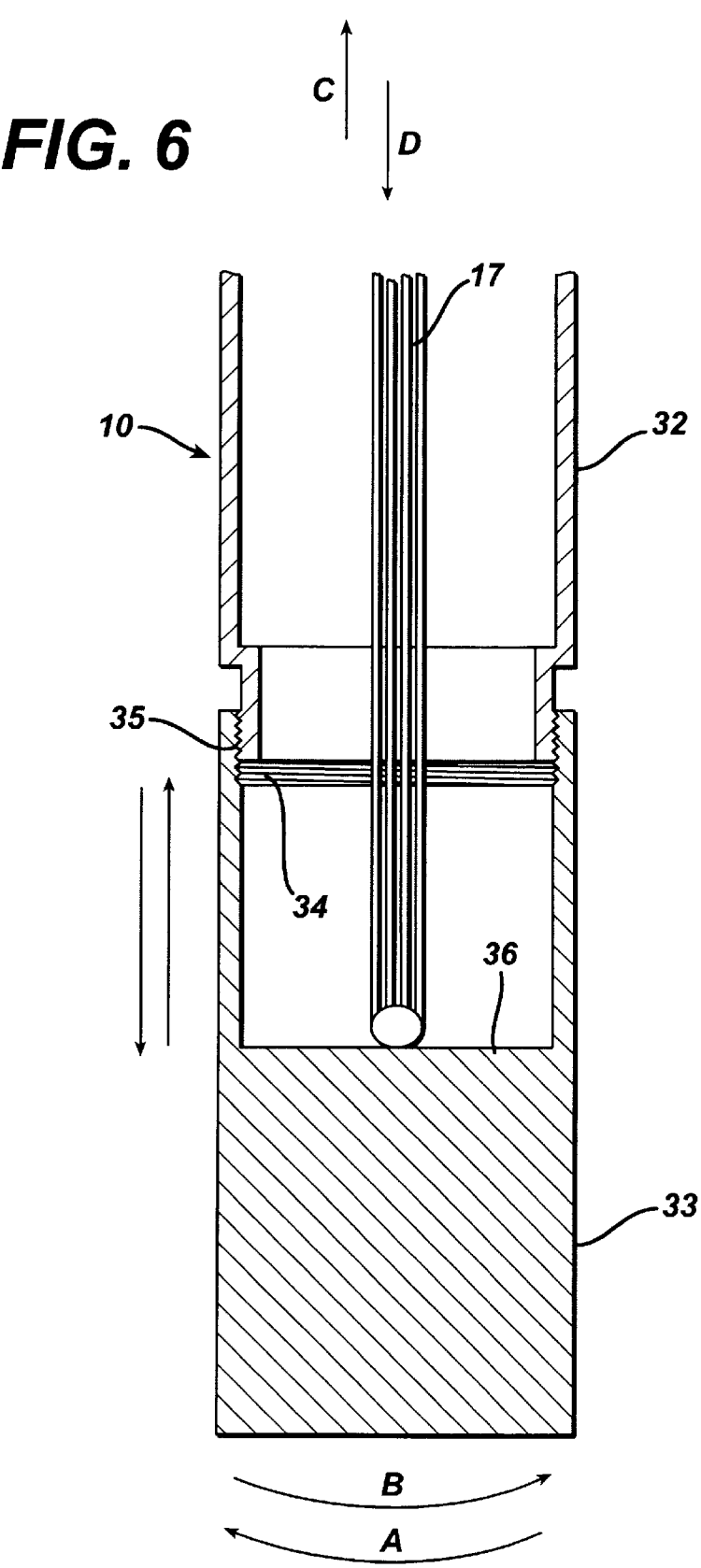
FIG. 6 is a partly cross-sectional view of a control handle for the invention.

FIG. 6 depicts a control handle especially suitable for the embodiment of the invention shown in FIGS. 5A and 5B. The proximal end 32 of guidewire 10 is rotatably attached to handle 33, such that rotation of handle 33 causes handle 33 to move distally or proximally relative to proximal guidewire end 32. For example, handle 33 may have threads 34 which engage threads 35 on guidewire proximal end 32. Fibers 17 attached to filter membrane 20 are secured in a base 36 of handle 33. Then, as handle 33 is turned, the fibers 17 move distally or proximally to open or close filter membrane 20.

As handle 33 is turned clockwise in the direction of arrow A and fibers 17 are allowed to move distally in the direction of arrow C, the tension on the filter membrane fibers 17 decreases and wires 51 are allowed to assume their natural 90° angle with respect to the guidewire, resulting in opening of filter membrane 20. Similarly, when handle 33 is turned counter-clockwise in the direction of arrow B and fibers 17 are pulled proximally in the direction of arrow D, the tension on filter fibers 17 increases, causing filter membrane 20 to collapse tightly against guidewire 10. Of course, the direction of turn of handle 33 as discussed above can be reversed, as long as threads 34,35 are properly formed to allow appropriate movement of handle 33 relative to guidewire proximal end 32.

Figure 11:
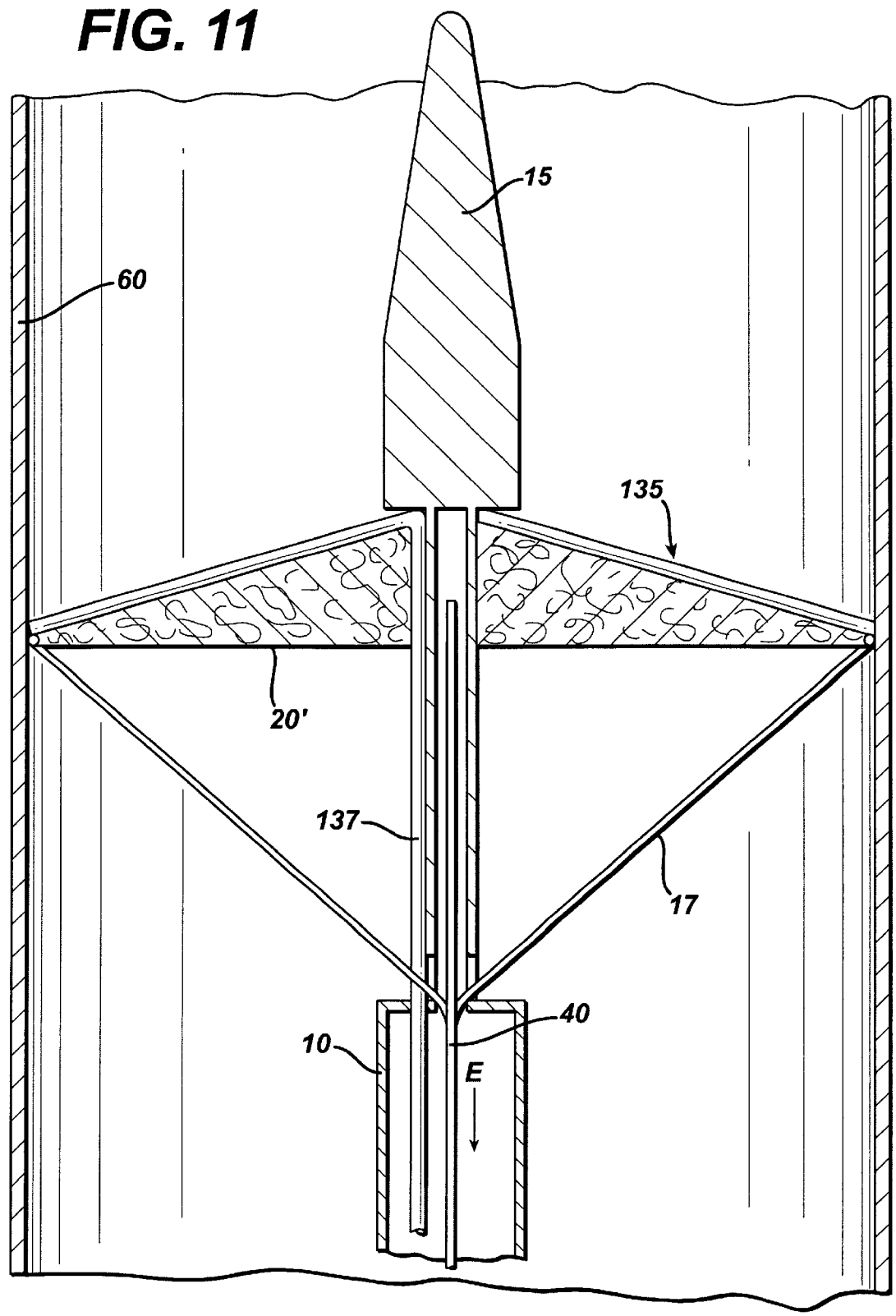
FIG. 11 is a partial cross-sectional view of another embodiment of the invention having inflatable support spines.

In yet another embodiment of the invention, shown in FIG. 11, filter membrane 20 can be supported by inflatable spines 135 supporting the filter membrane 20. Spines 135 supporting the filter membrane 20 are from two, to six hollow plastic tubes which are inflatable using, for example, a standard balloon angioplasty inflation device or endoflator in fluid connection through channel 137 with spines 135. Inflation of spines 135 causes them to become rigid and deploys filter membrane 20. The underside of the filter membrane is attached to very thin fibers 17 which are attached to moveable core 40 inside hollow guidewire 10. Filter membrane 20 is collapsed by deflating the spines 135 and withdrawing the moveable core 40 in the direction of arrow E until the membrane 20 fits tightly against guidewire 10.

Figure 7:
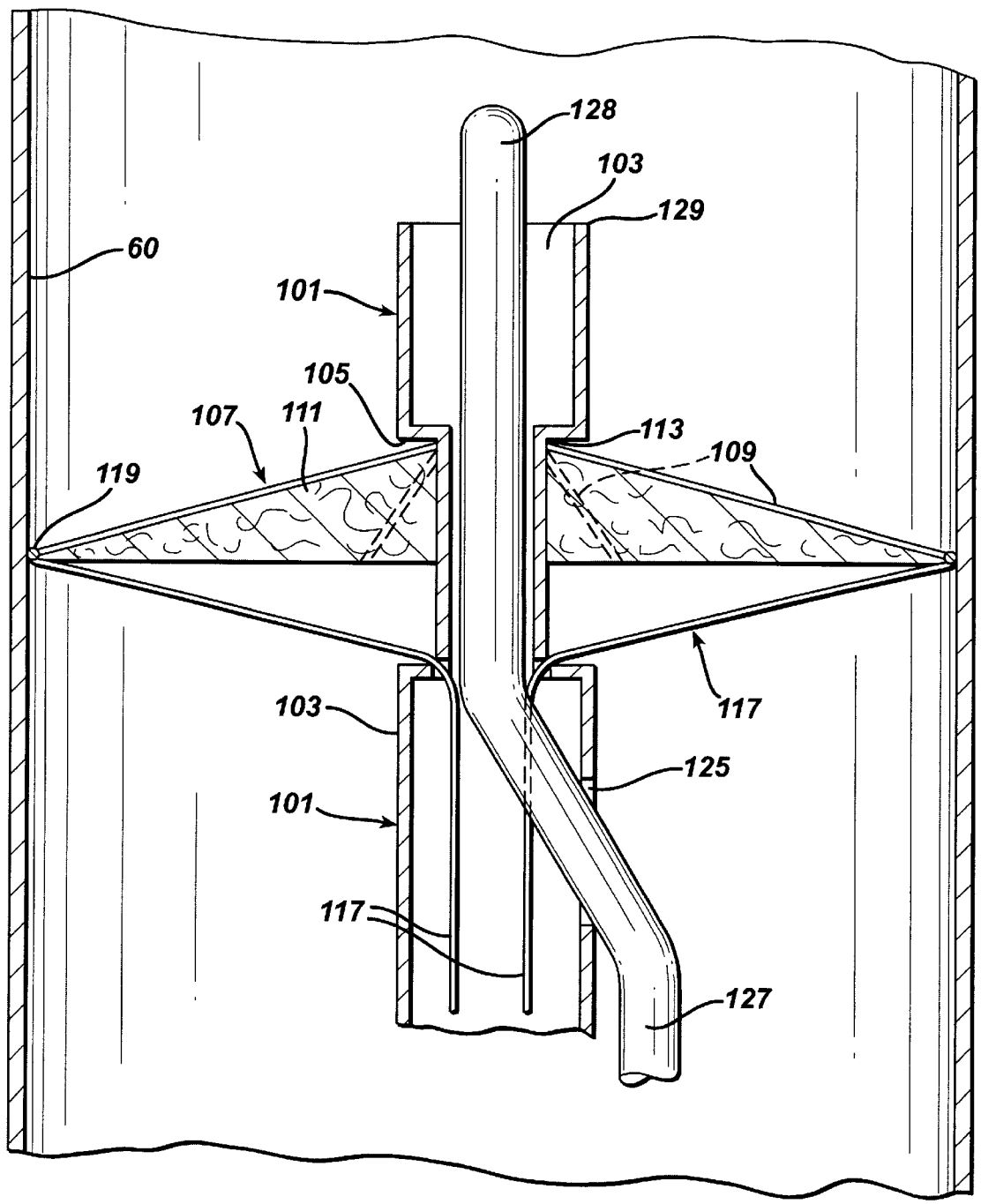
FIG. 7 is a partly cross-sectional view of another embodiment of the invention.

A catheter-based configuration is also possible, as shown in FIG. 7. In this design, the guidewire is not part of the filter catheter; the guidewire and filter catheter are two separate components. The filter catheter has an entry hole for the guidewire below the attachment of the filter membrane and the guidewire exits out the end of the filter catheter. The filter catheter could be designed to accommodate a variety of guidewire sizes, most commonly a 0.014 inch guidewire. The advantages of this design are that a variety of guidewires could be used; the lesion could be crossed with the guidewire prior to crossing with the filter catheter; the filter catheter could be removed from the artery without removing the guidewire; and the filter catheter could be made smaller.

In the embodiment of the invention shown in FIG. 7 a catheter 101 comprises a longitudinally extending lumen 103, which has an annular recess 105 adjacent the distal end of catheter 101. Positioned within recess 105 is a filter 107 comprised of structural wires 109 and a filter membrane 111. The distal end of each of wires 109 is attached at point 113 in recess 105. Fibers 117 extend from the proximal ends 119 of wires 109 proximally to a control means such as described in FIG. 6.

Catheter 101 contains guidewire port 125 located proximal to recess 105. It is intended that in use the distal portion 128 of a guidewire 127 will be threaded into the distal end 129 of catheter 101 and out through port 125.

Alternatively, and not shown here, a catheter 101 could comprise a longitudinally extending lumen and a shorter tracking lumen that extends from distal end 129 to a point proximal to recess 105. The distal end of guidewire 127 would then be threaded into the distal opening of the tracking lumen and out the proximal end of the tracking lumen.

Figure 8:
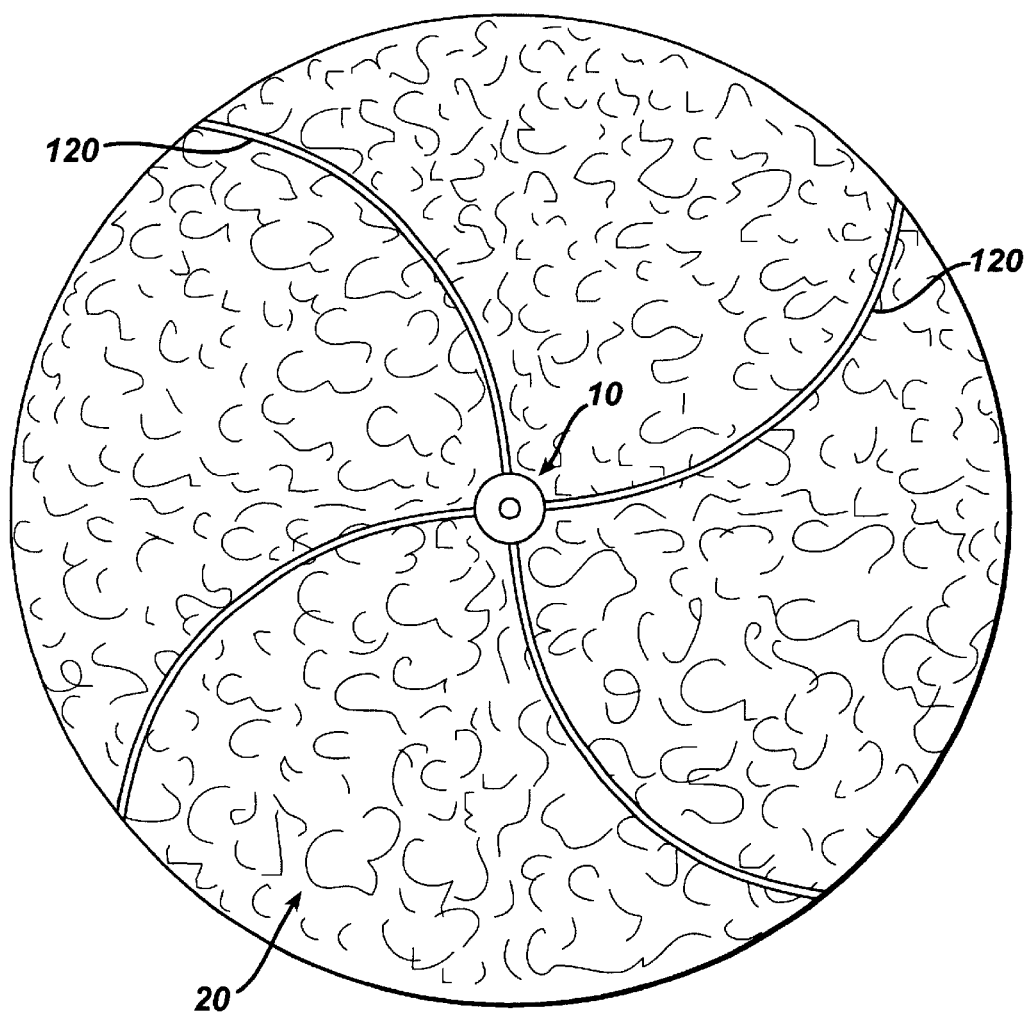
FIG. 8 is a partial cross-sectional view of an embodiment of the invention wherein the filter membrane has curved supports.

Spiral or curved structural wires may be used to deploy the filter membrane instead of straight wires. FIG. 8 illustrates the use of four curved wires 120. The angulation of the filter attachment point of wires 120 relative to their guidewire attachment has the effect of wrapping the filter fabric around the guidewire in the undeployed state. This leads to a lower profile for the undeployed filter.

Figure 9:
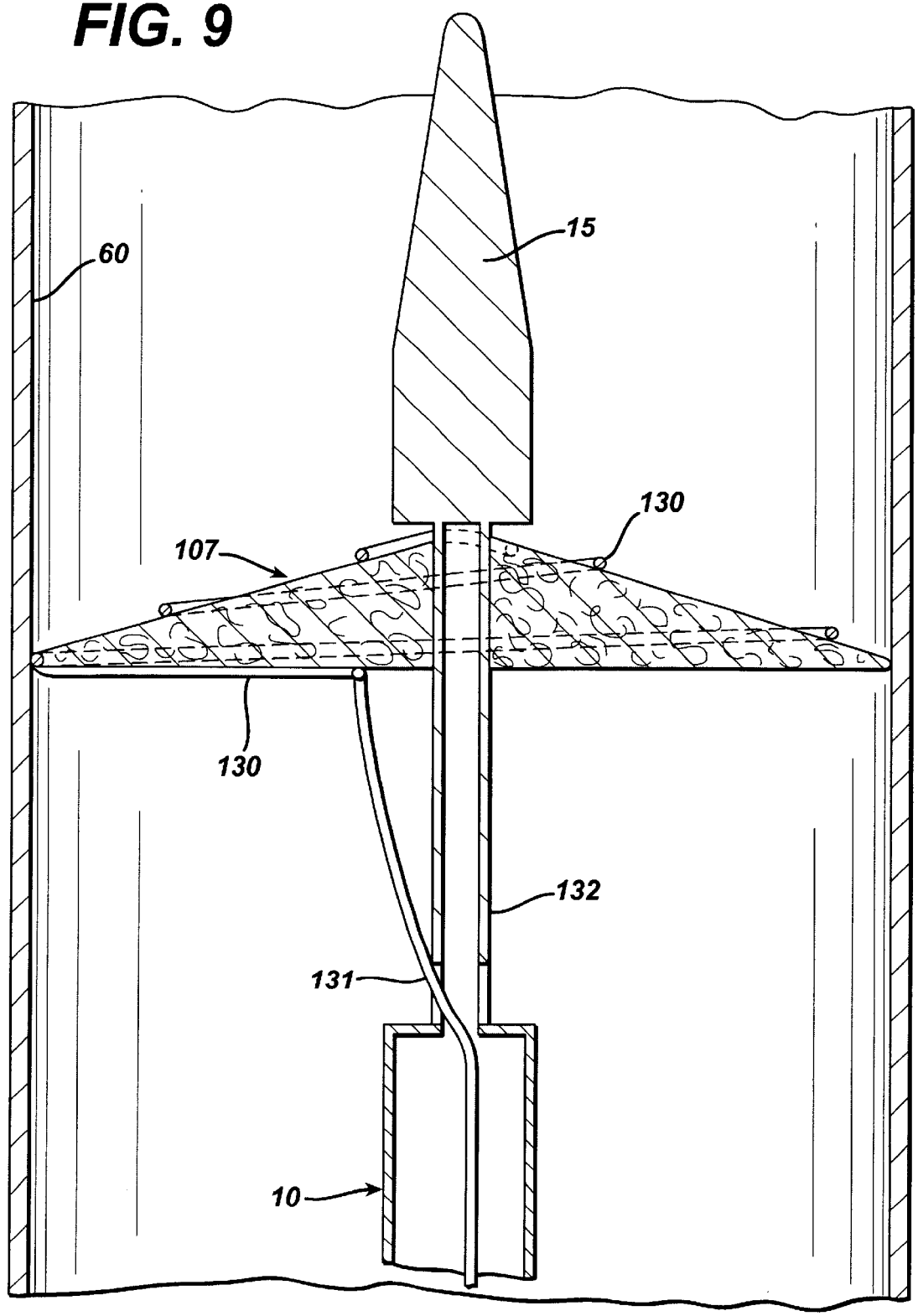
FIG. 9 is a partial cross-sectional view of yet another embodiment of the invention wherein the filter membrane has a spiral wire.
Figure 10:
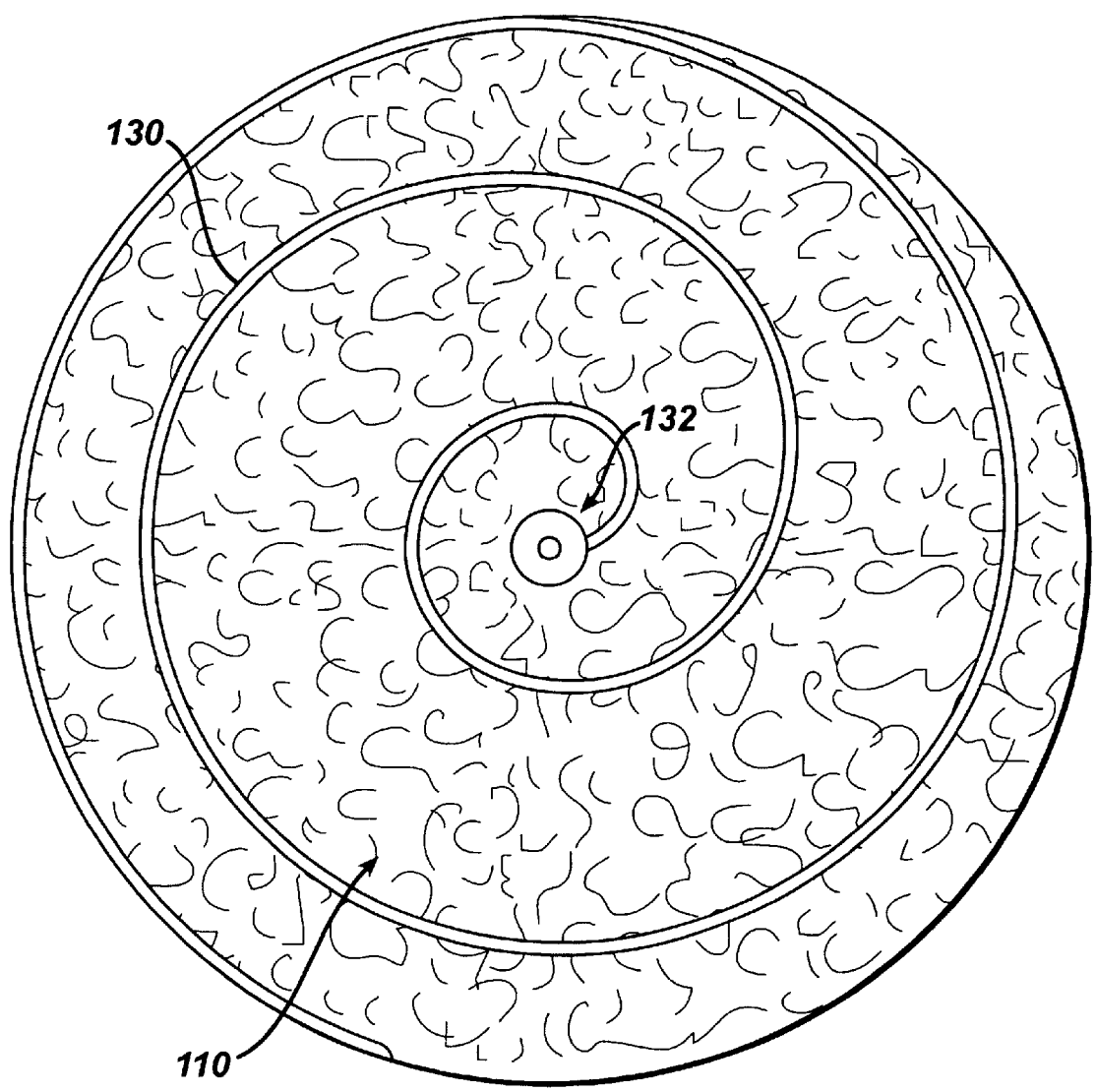
FIG. 10 is a top, cross-sectional view of the embodiment of the invention shown in FIG. 9.

FIGS. 9 and 10 illustrate the use of a single spiral structural wire 130 which is attached to the filter 107. As tension fiber 131 is released, wire 130 unwinds and deploys filter 107 in a conical configuration. This configuration has the simplicity of using a single wire and, when the tension on fiber 131 is increased, allows filter 107 to be wrapped very tightly around the guidewire shaft 131, resulting in filter 107 having a low profile in its undeployed state.

Figure 12:
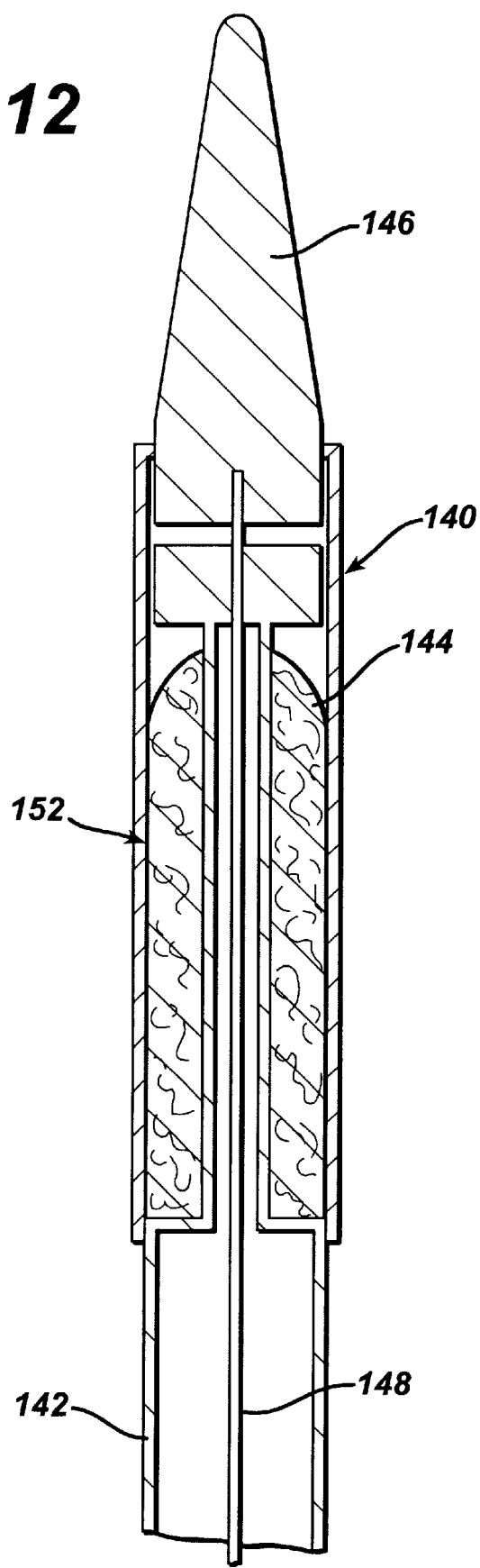
FIGS. 12 and 13 represent partial cross-sectional views of another embodiment of the invention in collapsed and deployed positions, respectively.
Figure 13:
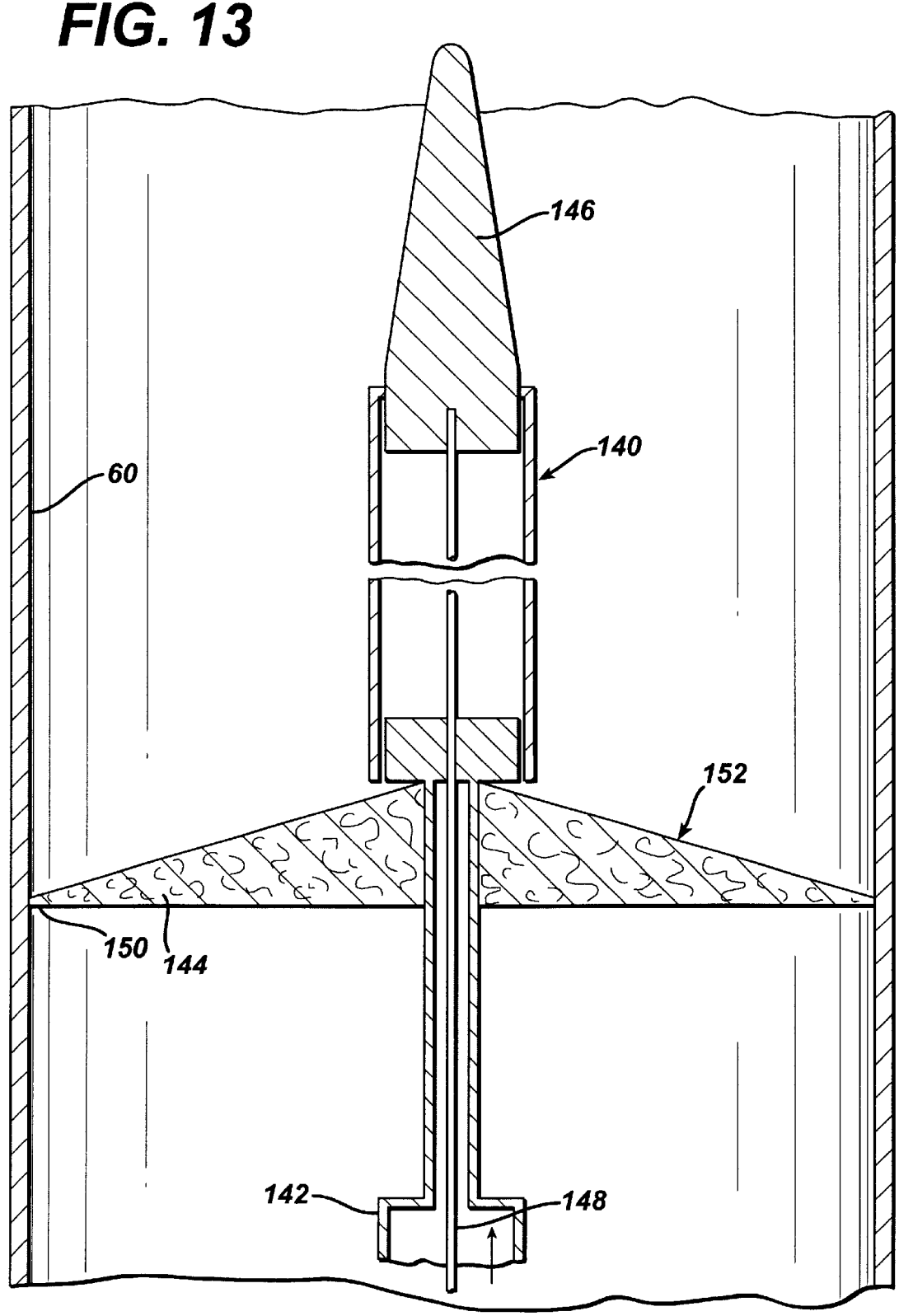

Another modification shown in FIGS. 12 and 13 comprises a retractable sheath 140 at the distal end of guidewire 142 which covers filter membrane 144 in the collapsed state. Sheath 140, the distal portion of which is affixed to guidewire tip 146, which is affixed to the distal end of moveable core 148, would prevent an edge 150 of filter membrane 144 from becoming entangled in an artery or guide catheter as it was being withdrawn from a patient.

More specifically, when guidewire 142 with tapered tip 146 is inserted percutaneously into a patient, sheath 140 covers collapsed filter membrane 144. After the filter membrane is determined by fluoroscopy to be in proper position, moveable core 148 is pushed distally to cause sheath 140 to "release", filter membrane 144, which has spines 152, to cause filter membrane 144 to deploy, as shown in FIG. 13.

It will be seen that the objects set forth above, among those made apparent from the preceding description, are efficiently attained and, since certain changes may be made in carrying out the method and in the apparatus set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features herein and described and all statements of the scope of the invention which, as a matter of language, might be said to fall therebetween.

ITEM LISTING

No. Item
10 Guidewire
11 Guidewire lumen
12 End of collapsing fiber
13 End of collapsing fiber
14 Filter membrane outer edge
15 Guidewire soft tip
17 Collapsing fiber
18 Attachment point
20 Filter membrane
22 Filter membrane attachment point
24 Filter membrane fixed portion
27 Fiber attachment point
28 Fiber attachment point
30 Deploying fibers
32 Guidewire proximal end
33 Handle
34 Handle threads
35 Guidewire proximal end threads
36 Handle base
40 Moveable core wire
50 Structural wires
51 Deploying wires
60 Artery wall
101 Catheter
103 Lumen
105 Recess
107 Filter mesh structure
109 Filter wire
111 Mesh
113 Attachment point
117 Deployment collapse wire
120 Curved filter structural wires
125 Guidewire port
127 Guidewire
128 Guidewire distal end
129 Spiral wire
131 Fiber
132 Guidewire shaft
135 Inflatable spines
137 Inflation channel
140 Sheath
142 Guidewire
144 Filter member
146 Tapered guidewire tip
148 Moveable core
150 Filter membrane edge
152 Filter membrane spine

I claim:

1. A removable percutaneous vascular filter device for capturing micro-and macro-emboli while allowing continued perfusion of blood, comprising:

a guidewire comprising an elongate member having distal and proximal portions, the distal portion including a shapeable, tapered soft distal tip, an outside diameter, and a recess in the distal portion immediately adjacent the distal tip, the recess having distal and proximal ends, and a predetermined depth, the guidewire further comprising a central lumen;

a filter comprising (a) a non-metallic, porous, flexible filter membrane having a distal portion and a proximal free end portion and (b) a filter membrane support structure extending from the flexible filter membrane distal portion to at least the flexible filter membrane proximal portion, wherein said filter membrane distal portion is pivotally attached to the guidewire near said distal end of the guidewire recess and wherein the filter membrane proximal free end portion is positioned in the recess substantially parallel to the guidewire when the filter membrane is in a collapsed state, the predetermined depth of the recess providing a space wherein the filter membrance lies adjacent to an inner portion of the elongate member when the filter membrane is in the collapsed state and has an outside diameter that is less than the outside diameter any portion of of the elongate member except for said recess and the distal portion of said distal tip; and deploying means operatively connected to the filter to cause filter membrane proximal free end portion to move from a position substantially parallel to the elongate member to a position removed from the longitudinal axis of the elongate member to cause the flexible filter membrane to form a substantially conical shape to form a generally sealing relationship with the wall of said vessel, the deploying means including a moveable core being slidably positioned in the central lumen and extending beyond the flexible filter membrane distal position and into the shapeable, tapered soft distal tip.

2. The vascular filter of claim 1, wherein the pore size of the filter membrane is from about 40 to about 300 microns.

3. The vascular filter of claim 1, wherein the deploying means further comprises deploying fibers each having first and second ends and said filter membrane further comprises an outer edge, and wherein said deploying fibers are each attached at a first end to the moveable core and are attached at a second end to the outer edge of the filter membrane.

4. The vascular filter of claim 3, wherein the moveable core creates a tension in the deploying fibers when it slides proximally in relation to the guidewire, and said tension causes the filter membrane to expand outwardly until the outer edge of the filter membrane is in firm contact with a lumen wall.

5. The vascular filter of claim 3 further comprising a means for collapsing the filter membrane from a deployed state to a collapsed state.

6. The vascular filter of claim 5, wherein the collapsing means further comprises collapsing fibers each having first and second ends, wherein said collapsing fibers are each attached at a first end to the moveable core and are further attached at a second end to the outer edge of the filter membrane.

7. The vascular filter of claim 6, wherein the moveable core creates a tension in the collapsing fibers when it slides proximally in relation to the guidewire, the said tension causes the filter membrane to collapse tightly against the guidewire.

8. The vascular filter of claim 1, wherein the lumen extends distally from the proximal portion of the guidewire to at least the recess.

9. A removable percutaneous vascular filter device for capturing micro- and macro-emboli while allowing continued perfusion of blood, comprising:

a guidewire comprising an elongate member having distal and proximal portions, the distal portion including a shapeable, tapered soft distal tip, an outside diameter, and a recess in the distal portion immediately adjacent the distal tip, the recess having distal and proximal ends, and a predetermined depth;

a filter comprising a non-metallic, porous, flexible filter membrane and a filter membrane support structure, the filter membrane having a fixed inner portion and a free outer portion, wherein the filter membrane fixed inner portion is attached toward the distal end of the recess and wherein the filter membrane free outer portion is positioned in the recess when the filter membrane is in a collapsed state, the predetermined depth of the recess providing a space, wherein the filter membrane lies adjacent to an inner portion of the elongate member when the filter membrane is in the collapsed state and has an outside diameter that is less than the outside diameter any portion of of the elongate member except for said recess and the distal portion of said distal tip and wherein the filter membrane in an unstressed position assumes a position substantially normal to the longitudinal axis of the elongate member; and means operatively connected to the filter to collapse the filter membrane from a deployed state to a collapsed state.

10. The vascular filter of claim 9, wherein the filter membrane comprises wires which assume a 90° angle with respect to the longitudinal axis of the guidewire in an unconstrained state.

11. The vascular filter of claim 9, wherein the filter membrane comprises from 2 to 6 arcing wires.

12. The vascular filter of claim 9, wherein the filter membrane comprises a single spiral wire.

13. The vascular filter of claim 9, wherein the collapsing means comprises collapsing fibers each having first and second ends, wherein said collapsing fibers are each attached at a first end to the outer edge of the filter membrane and the second end of each fiber extends proximally through the guidewire to an actuator.

14. The vascular filter of claim 13, wherein the actuator is a handle or shaft that can be rotated clockwise or counter-clockwise to release or collapse the filter membrane.

15. The vascular filter of claim 9, wherein the filter membrane comprises a set of inflatable spines, said spines being hollow plastic tubes.

16. The vascular filter of claim 15 which further comprises an inflator for inflating the spines, wherein said inflator is in fluid communication with said spines, which become rigid upon inflation.

17. The vascular filter of claim 16, where the means of inflation is an endoflator.

18. The vascular filter of claim 9, wherein the guidewire has a lumen extending distally from the proximal portion of the guidewire to at least the recess.

19. The vascular filter of claim 9, which also comprises a sheath positioned concentric to the collapsed filter membrane, wherein said membrane causes the filter member to be in a collapsed state but can be moved distally to allow the filter member to extend radially.

20. The vascular filter of claim 19, wherein the sheath has proximal and distal portions and is attached at its distal end to a distal guidewire tip that is affixed to a moveable core extending proximally through the guidewire.

* * * * *